United States Patent
Van Den Eerenbeemd et al.

(10) Patent No.: US 8,364,257 B2
(45) Date of Patent: Jan. 29, 2013

(54) WEARABLE DEVICE AND SYSTEM FOR A TAMPER FREE ELECTRIC STIMULATION OF A BODY

(75) Inventors: Jacobus Maria Antonius Van Den Eerenbeemd, Eindhoven (NL); Dirk Brokken, Eindhoven (NL); Willem Franciscus Johannes Hoogenstraaten, Eindhoven (NL); Roel Reusens, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 121 days.

(21) Appl. No.: 12/996,416

(22) PCT Filed: Jun. 16, 2009

(86) PCT No.: PCT/IB2009/052549
§ 371 (c)(1),
(2), (4) Date: Dec. 6, 2010

(87) PCT Pub. No.: WO2009/153730
PCT Pub. Date: Dec. 23, 2009

(65) Prior Publication Data
US 2011/0087300 A1   Apr. 14, 2011

(30) Foreign Application Priority Data
Jun. 19, 2008   (EP) .................................. 08158546

(51) Int. Cl.
*A61N 1/00* (2006.01)

(52) U.S. Cl. ............................................ 607/2
(58) Field of Classification Search ............... 607/2
See application file for complete search history.

(56) References Cited

U.S. PATENT DOCUMENTS

| | | | |
|---|---|---|---|
| 4,088,141 A | 5/1978 | Niemi | |
| 4,328,814 A | 5/1982 | Arkans | |
| 4,769,881 A | 9/1988 | Pedigo et al. | |
| 5,048,522 A | 9/1991 | Petrofsky | |
| 5,697,955 A * | 12/1997 | Stolte | 607/5 |
| 2003/0097125 A1 | 5/2003 | Hall | |
| 2004/0229702 A1 | 11/2004 | Cooke | |
| 2007/0038257 A1 | 2/2007 | Gray | |
| 2007/0106343 A1 | 5/2007 | Mongue et al. | |

FOREIGN PATENT DOCUMENTS

| | | |
|---|---|---|
| DE | 10353970 A1 | 7/2005 |
| EP | 1486164 A1 | 12/2004 |
| GB | 2424595 A | 10/2005 |
| WO | 02078559 A1 | 10/2002 |

* cited by examiner

*Primary Examiner* — George Manuel

(57) ABSTRACT

A wearable device or electric stimulation of a users body fits a portion of the user's body and includes at least one electrode embedded in the wearable device transferring a stimulating current to the user's body. A connection point is an intermediate connection between the at least one electrode and a control unit. The control unit is configured to generate the stimulating current. A detector is configured to detect if a change in a physical relationship between the connection point and the at least one electrode exceeds a predetermined threshold value, thereby enabling detection of misuse and tampering with the device.

20 Claims, 2 Drawing Sheets

WEARABLE DEVICE AND SYSTEM FOR A TAMPER FREE ELECTRIC STIMULATION OF A BODY

TECHNICAL FIELD

The present invention relates to a wearable device for electro stimulation of a user's body.

BACKGROUND OF THE INVENTION

Electro stimulation is a promising new way to address the human neurological systems, and can be exploited for a wide range of medical and non-medical applications such as for example pain-relief, galvanic vestibular stimulation, muscle stimulation, and sensory stimulation. Electro stimulation techniques are currently mostly used for medical treatment, under supervision of a qualified medical professional. However, a trend can be seen suggesting that electro stimulation may become a mainstream modality in other fields as well, where a qualified medical professional is not always available. Examples thereof are devices for home healthcare or devices for use with computer games.

GB 2424595 discloses a computer game accessory which connects to and receives digital instructions from a computer and as a result produces electrical pulses which are fed to pads attached to a players body for the purpose of producing electro stimulation to the players muscles thereby adding physical effects to the game experience. Such a device could be used to add physical effects to the game experience (e.g. if the player is shot in the game he could be exposed to electrical pulses to simulate pain) provided that a player attaches the pads on his body the way he is supposed to.

However, in a competitive computer game (e.g. online gaming) a participant may be tempted to cheat by avoiding or reducing the intended electro stimulation thereby unduly appropriate himself a competitive advantage. Furthermore, it is also obvious that improper use of electro stimulation may be harmful to the user. For example, electro stimulation of the heart may lead to heart failure.

Thus, in view of the above, an object of the invention is to prevent misuse of a device for electro stimulation of a user's body, and more specifically prevent tampering with the device.

SUMMARY OF THE INVENTION

According to an aspect of the invention, the above object is met by a wearable device for electric stimulation of a user's body, wherein the wearable device is adapted to fit a portion of the user's body, the wearable device comprising at least one electrode embedded in the wearable device for transferring a stimulating current to the user's body, a connection point being an intermediate connection between the at least one electrode and a control unit, the control unit being adapted to generate the stimulating current, and means for detecting if a change in a physical relationship (e.g. an electrical relationship such as a change in resistance, capacitance, inductance, and/or impedance or a relative relation such as a distance) between the connection point and the at least one electrode exceeds a predetermined threshold value, thereby enabling detection of misuse and tampering with the device.

As the wearable device is specifically adapted to fit a portion of the user's body, the user is prevented from unintentionally placing the electrodes on other parts of the body. This ensures no harm is done to the user, for example, by placing the electrodes in such a way that a risk of stimulating the heart exists which may lead to a heart failure. This may be advantageous in applications such as, for example devices for home healthcare or computer game applications. Furthermore, intentional misuse such as tampering with the electrodes or its related circuitry, stretching the wearable device to make it fit a part of the body for which it is not intended, or dismantling of the device to such an extent that the electrodes can be placed over unwanted regions (e.g. chest, head) can be detected and the electro stimulation can be disabled. In addition, device failure such as device wear leading to component failure or unintended failure of the device hardware components may also be detected. The arrangement also enables an anti-cheat functionality so that all players participating in a competitive computer game, such as online gaming, experience identical challenge levels.

Tampering with the device here should be interpreted broadly and may refer to any modification done to the wearable device, its electrodes or the related circuitry which may enable the device to provide electro stimulation in a way that is not intended or to a portion of the body which is not intended. Also, a change in the physical relationship between the connection point and the at least on electrode here should be interpreted broadly. It may for instance relate to detecting a change in distance and/or relative position between the connection point and the electrode, but may also relate to an electrical relationship such as e.g. a change in resistance, capacitance, inductance, and/or impedance in a connection between the connection point and the electrode. The connection point may be an imaginary point on an electrical wire connecting the electrode to the control unit, or a physical point such as, for example, a connector for connecting the electrodes to the control unit. The predetermined threshold value should be set in a way that tampering may be detected, while the wearable device remains robust to changes that may occur during normal operation, such as changes due to muscle contraction or due to changes in temperature.

Electro stimulation here refers to all kind of neuromuscular stimulation including electrical stimulation of muscles, muscle parts, muscle groups, nerves or combinations thereof. Examples are Transdermal Electro Nerve Stimulation (TENS) and Functional Electrical Stimulation (FES). Typical applications would be pain-relief, galvanic vestibular stimulation, muscle stimulation, and sensory stimulation.

An electrode here refers to any kind of conductor used to transfer a stimulating current to the user's skin. The electrodes are typically arranged in pairs, where each electrode pair comprises an electrode a having a first pole and an electrode having an opposite pole, such as an anode and a cathode. It is recognized that more than one electrode having a first pole can share an electrode having a second pole. Thus, for example, two electrodes having a first pole, and one electrode having a second pole may form two electrode pairs.

The present invention is based on the understanding that an attempt to tamper with the wearable device or the electrodes and its related circuitry changes the physical relationship between the connection point and the at least one electrode. Furthermore by providing a wearable device specifically adapted to fit a portion of the user's body, an attempt to fit the wearable device to other body regions will also change the physical relationship between the connection point and the at least one electrode.

The wearable device may comprise at least one electrical wire embedded in the wearable device, providing a connection from the connection point to the at least one electrode, wherein a length of the at least one electrical wire is at least twice a distance between the connection point and the electrode. An advantage is that a longer electrical wire can be arranged over a larger area of the wearable device, making it more difficult to dismantle the wearable device and/or its electrodes without cutting or in other way affecting the electrical wire. For example, rather than arranging the electrical wire along a straight line from the connection point to the electrode, the electrical wire could be arranged in an S-shaped pattern for example embedded in or arranged on the surface of the wearable device.

The wearable device may encompass the portion of the user's body which the wearable device is adapted to fit. An advantage is that the device will typically not fit another (e.g. larger) portion of the body. In particular, if the wearable device is adapted to fit the arm of a user, and thus adapted to encompass or encircle the arm, it will not fit over the head or the chest without changing the physical relationship between the connection point and the electrode (for example by stretching the wearable device), why any attempt to do so will be detected. This is an efficient way to protect the user from harm as the areas of the body where it may be dangerous to apply electro stimulation typically are the heart-area (i.e. the chest) and the head, each having a rather large circumference.

The at least one electrical wire may be circumferentially arranged such that it is adapted to encompass the portion of the user's body. The result is an even more efficient way to prevent tampering or dismantling of the wearable device and/ or its electrodes. For example, if the wearable device is adapted to fit and encircle the arm, the electrical wire may be circumferentially arranged in a helical shape around the hollow core of the wearable device. Thus, any attempt to cut open the wearable device, for example to make it fit over the head, typically will cut off the electrical wire.

The wearable device may be a sleeve-shaped wearable device adapted to fit a portion of the user's arm or leg. An advantage is that the device cannot be used for electro stimulation of other areas of the body, such as the head or chest region, which may be dangerous. The sleeve-shaped wearable device may preferably be adjustable and/or stretchable to accommodate different body sizes. For example, a sleeve-shaped wearable device for use on an arm may have a diameter adjustable between 5 and 10 cm.

The wearable device may be a garment such as a jacket, a vest, a glove, a sock, a pair of trousers or a cap. An advantage by embedding the electrodes in a garment is that as the user takes on the garment, the electrodes will be arranged at predetermined positions of the user's body intended for electro stimulation. It is recognized that, as a cap is worn on the head such a device would typically be used for galvanic vestibular stimulation, rather than TENS. Furthermore, socks and gloves would typically be of interest to stimulate sensations (e.g. pain) rather than for muscle stimulation.

The wearable device may be openable and provided with means usable to ensure that the wearable device is closed before the stimulating current is provided. An openable device may be convenient as a user takes on and off the wearable device, while misuse, such as arranging the device on a part of the body where it only partly fits, is prevented. For example, an electric switch could be provided which closes the circuit between the control unit and the electrodes when the wearable device is closed.

According to an embodiment of the invention, the control unit contains a predetermined reference key, wherein the control unit is adapted to measure a parameter for the at least one electrical wire (and/or for a sensing wire), and to calculate a key based on the at least one measured parameter, wherein the calculated key is usable for ensuring proper functioning of the wearable device by comparing the calculated key with the reference key.

The reference key may advantageously be a physically unclonable function (PUF). The electrodes and the associated electrical wires can be configured in such a way that a Physically Unclonable Function (PUF) arises which can be used by the control unit to recognize a tampering attempt. A set of parameters such as electrical characteristics of the electrical wires (e.g. capacitance, inductance, and resistance between the different wires at different frequencies) can be measured before the wearable device leaves the factory. From these measured parameters a unique key can be derived for that particular device which is stored in the control unit. The nature of the PUF is such that, although the unique key is easily measured, it would be very hard to construct another device that provides the same measurement results. Furthermore, a ratio between a measured parameter for a first electrical wire and a measured parameter for a second electrical wire may be used to calculate the key, wherein the second electrical wire is advantageously an electrical wire arranged near the first electrical wire. Employing a ratio enables electrical characteristics that are robust to normal changes that typically may occur in operation such as stretching of the cloth while applying the device to for example the lower-arm or changes in temperature. The two wires can preferably have sufficient "overlap" to create a large enough, i.e. measurable, parasitic capacitance, inductance, and resistance between the two measured wires.

The wearable device may comprise an additional sensing wire monitored by the control unit. By electrical monitoring of the additional sensing wire integrated in the wearable device, it is possible to stop electro stimulation, for example, as the resistance or impedance change significantly. This further enhance the ability to detect tampering with the device. The additional sensing wire may be circumferentially arranged.

The electrical wires (and/or the sensing wires) may cross one another while remaining electrically insulated. This can be achieved by arranging each electrical wire in a different layer in such a way that they remain electrically insulated, or by providing the electrical wires with an insulating coating. By crossing the electrical wires it will be even more difficult to dismantle the wearable device and/or its electrodes without cutting an electrical wire.

A plurality of sensing wires (and/or electrical wires) may be arranged in a mesh usable to locate a change in position of the at least one electrodes, for example by measuring the parasitic capacitance, inductance, and resistance between the wires. Furthermore, by meshing the wires in a random fashion during fabrication the parasitic capacitance, inductance, and resistance between the different electrodes can form a PUF.

Each electrical wire and/or each sensing wire may be arranged in a different layer in such a way that the wires cross one another while remaining electrically insulated. An advantage is that the material separating the wires can be part of generating the PUF since the material properties (such as the permittivity) vary spatially in a random fashion by the way it is manufactured.

The wearable device may comprise at least one sensor configured to detect contact with the user's skin, whereby the device is operable only if a predefined portion of the wearable device makes contact with the skin. An advantage is that it may be ensured that the wearable device is properly fitted to the user's body, and it would prevent use of the device on an unintended body part, which only partly fits the wearable device. It may also be used to ensure that the wearable device is actually in contact with the skin of the user and not some other material.

Additionally, a wearable device for transferring the stimulating current to the user's body may together with a control unit form a system for electrically stimulating a user's body, wherein the control unit is adapted to control the electrodes and to detect tampering with the wearable device.

Other objectives, features and advantages will appear from the following detailed disclosure, from the attached dependent claims as well as from the drawings.

BRIEF DESCRIPTION OF THE DRAWINGS

These and other aspects of the present invention will now be described in more detail, with reference to the appended drawings showing currently preferred embodiments of the invention, in which.

DETAILED DESCRIPTION OF PREFERRED EMBODIMENTS

Figure 1A:
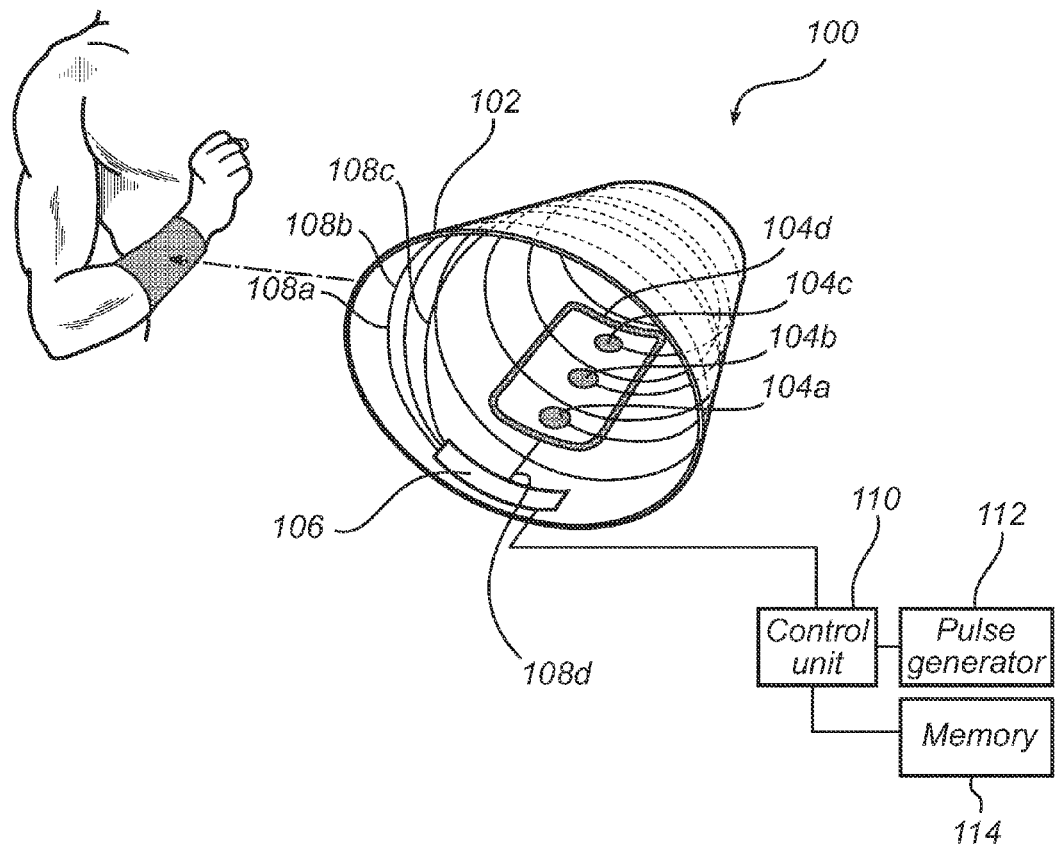
FIG. 1a illustrates a sleeve-shaped TENS-device for electro stimulation of a user's lower arm.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Referring now to the drawings and to FIG. 1a in particular, there is depicted a wearable TENS (Transdermal Electro Nerve Stimulation)—device 100 for electro stimulation of a user's lower arm. The wearable TENS-device 100 here has the form of a tube-shaped sleeve 102 with a length about 20 to 30 cm, and a diameter adjustable (or elastic) between 5 and 10 cm to allow different body sizes to be accommodated.

The sleeve 102 is typically made of textile, but alternative materials that are deformable, electrically isolating and preferably also stretchable are possible, e.g various plastics. By using an elastic material in the sleeve 102 it could conveniently be thread onto the user's arm.

The wearable TENS-device 100 is provided with electrodes 104a-d embedded in the sleeve 102. The electrodes are typically made of electrically conducting rubber. An alternative would be to use metal or plastic electrodes plated with silver-chloride. The electrodes 104a-d are arranged on the skin facing side of the sleeve 102 to enable the electrodes 104a-d to engage with the skin of the user. Here, the electrodes 104a-d are three anodes 104a-c surrounded by a cathode 104d. The distance between the electrodes 104a-d typically vary between 2 to 5 cm. It is recognized by a person skilled in the art that the number of electrodes and the design thereof may vary depending on the application. The electrodes 104a-d, i.e. the anodes 104a-c and the cathode 104d, are connected to an intermediate connection point 106 by means of electrical wires 108a-d. In the illustrated example, each anode 104a-c is connected to the connection point 106 by a separate electrical wire 108a-c to enable individual control of each anode 104a-c.

The connection point 106 is connected to a control unit 110 and an associated pulse generator 112. Through the arrangement, the control unit 110 may selectively direct a stimulating current to the cathode 104d and/or one or more of the anodes 104a-c, wherein the duration and sequencing of the stimulating current applied to the user can be controlled. It should be noted that the electrodes typically are driven with an alternating current in such a way that the total injected current is equal in both directions. This prevents transcutaneous iontophoretic transport of e.g. salt and various other substances that are present on the skin as this may otherwise cause skin irritation. The control unit 110 may be arranged in an external unit, or be an integral part of the wearable TENS-device 100.

In the embodiment illustrated in figure 1a, the electrical wires 108a-c to the anodes are circumferentially arranged, wherein each of the electrical wires 108a-c that connects one of the anodes 104a-c to the connection point 106 is arranged in a helical shape around the hollow core of the sleeve 102. Here each electrical wire 108a-c is wound twice around the hollow core. In figure 1a it can be seen how the electrical wires 108a-c are distributed across the lateral surface of the sleeve 102 in a way that any attempt to dismantle the sleeve 102 and/or the electrodes 104a-d and the associated wiring most likely cuts off at least one of the electrical wires 108a-d.

Figure 1B:
FIG. 1b illustrates a wearable TENS-device in the form of a vest enabling electro stimulation of predetermined portions of the user's body.

In other embodiments it may not be desired or possible to have the electrical wires circumferentially arranged. If so, the electrical wires may be spread out across the surface of the wearable TENS-device 100 to achieve a similar effect. An example is a vest to be used with a computer game illustrated in FIG. 1b, where the electrical wires are arranged in an S-shaped pattern.

For the electrical wires 108a-d to remain electrically insulated as they cross one another, each electrical wires 108a-d may be provided with an insulating coating. As an alternative to insulating coating each electrical wire 108a-d can be arranged in a different layer of cloth (or any other material having similar characteristics) to remain electrically insulated as they cross one another. The latter alternative may be useful, for example, when using conductive yarns that can be interwoven with the cloth itself.

According to an embodiment, the control unit 110 performs an electrical detection of the state of the complete galvanic path to the skin before any stimulating current is applied to the user. This can be performed by sending a current to each anode 104a-c and measuring the resistance between that anode 104a-c and the cathode 104d. The current for skin resistance measurement is typically less than 0.1 µA (compared to 3 to 40 mA for stimulating motor nerve fibres using TENS depending on the duration of the stimulus) and thus is typically harmless to the user. When the wearable TENS-device 100 works properly and the electrodes 104a-d are properly attached to the skin, the measured resistance is typically about 5 to 50 MΩ although there may be some variation due to the presence of moisture and additive on the skin. However, if the measured resistance is substantially higher (e.g. 200 MΩ), this indicates that either there is no skin contact or a wire has been cut off, i.e. tampering with the system has occurred. If so the control unit 110 will disable the wearable TENS-device 100, and there will be no electro stimulation applied to the user. The resistance between the anodes 104a-c and the cathode 104d, is preferably measured repeatedly during operation of the wearable TENS-device 100.

Figure 2:
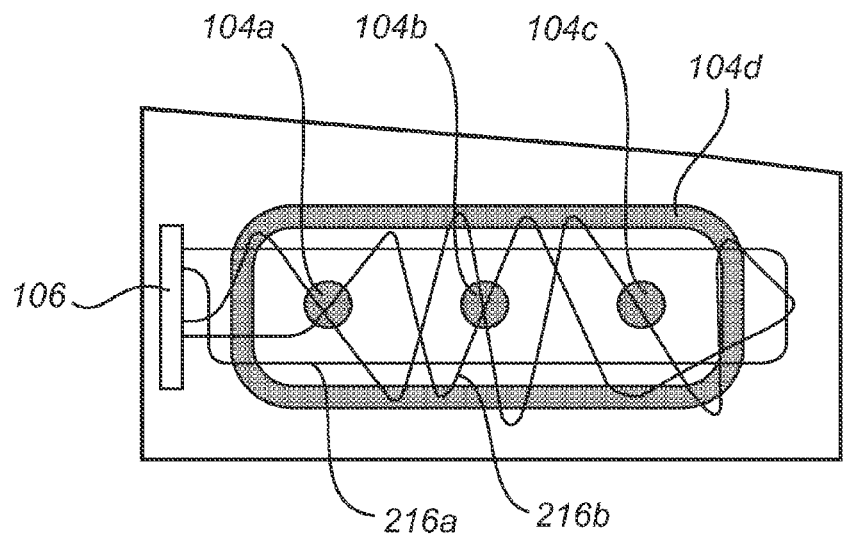
FIG. 2 illustrates a sleeve-shaped TENS-device provided with additional sensing wires arranged in a mesh to detect a change in the position of the electrodes.

FIG. 2 illustrates a wearable TENS-device 100 provided with two additional sensing wires 216a-b, which are separate from the electrical wires 108a-d used for driving the electrodes. Two wires are for illustrative purpose only and the number of wires may vary depending on the application. The sensing wires 216a-b are connected to the control unit 110 and thus can be monitored in a similar way as the electrical wires 108a-d driving the electrodes, thereby further enhancing the capability to detect misuse and tampering.

In the illustrated embodiment, the sensing wires 216a-b are arranged in a mesh, wherein the sensing wires cross one another multiple times. The shape of the mesh may vary and may or may not be random. In the event a user tries to tamper with the wearable TENS-device 100, by dismantling an electrode 104a-d or by excessive stretching of the sleeve 102, there will be a relative movement between sensing wires 216a-b in the mesh. By measuring the capacitance, inductance, and/or resistance between the sensing wires 216a-b making up the mesh this movement can be detected (i.e. physical variation) by the control unit 110, which may disable the electro stimulation. In a practical application it may often be advantageous to use more than two wires in the mesh. Furthermore, it is recognized that the electrical wires 108a-d driving the electrodes similarly may be arranged in a mesh, and that a mesh can comprise both electrical wires 108a-d and sensing wires 216a-b.

According to an embodiment of the invention, the electrodes 104 and the associated electrical wires 108a-d are configured in such a way that a Physically Unclonable Function (PUF) arises which can be used by the control unit 110 to recognize a tampering attempt. To implement a PUF, a set of parameters here being electrical characteristics of the electrical wires 108a-c (such as, for example, capacitance, inductance, and resistance between the different wires at different frequencies) are measured before the wearable TENS-device 100 leaves the factory. From these measured parameters a unique key is derived for that particular device which is stored in a memory 114 associated with the control unit 110. The nature of the PUF is such that, although the unique key is easily measured, it would be very hard to construct another device that provides the same measurement results. This may be due to random occurrences in the manufacturing process.

By meshing the wires of multiple electrodes in a random fashion during fabrication the parasitic capacitance, inductance, and resistance between the different electrodes form a PUF. According to an embodiment, the electrical wires 108a-d are woven through different layers of cloth in such a way that the wires cross one another at many different instances while remaining electrically insulated. As the material properties (i.e. permittivity) of the material separating the wires vary spatially in a random fashion by the way it is manufactured this can be part of generating the PUF. Furthermore, it is recognized that the sensing wires can also be used to implement a PUF.

In operation, the control unit 110 can check the wearable TENS-device 100, before any stimulating current is applied to the user, by measuring the same parameters and determining a new key based on these measurements. Any tampering with the wearable TENS-device 100 will change the measured key from the unique key stored in the memory 114. As a result the control unit 110 may disable the electro stimulation of the wearable TENS-device 100.

By using ratios of measured parameters between several closely spaced electrical wires, more robust electrical characteristics can be achieved that permit changes that typically occurs in normal operation of the wearable TENS-device 100 and which should be allowed. Examples of such allowable changes are, stretching of the cloth while applying the wearable TENS-device 100 to e.g. the lower-arm or temperature changes. The wires should have sufficient "overlap" to create a measurable parasitic capacitance, inductance, and resistance between the measured wires.

Figure 3:
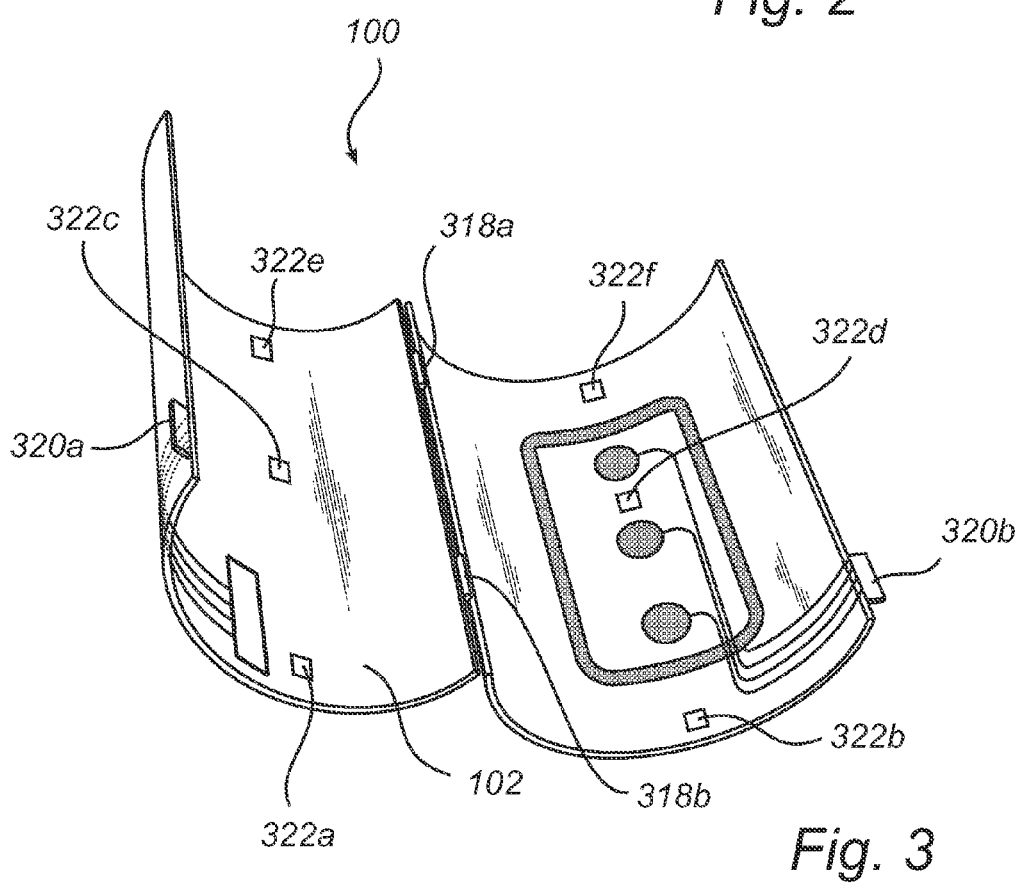
FIG. 3 illustrates an openable sleeve-shaped TENS-device.

According to another embodiment, the wearable TENS-device 100 is further provided with a set of sensors that can detect skin contact. The sensors may be mechanical, optical or electrical. By appropriate arrangement of the sensors it can be ensured that the wearable device is properly fitted to the user's body. In a sleeve-shaped TENS-device, sensors 322a-f may be arranged at both ends of the sleeve and in the middle of the sleeve as illustrated in FIG. 3 to ensure that the sleeve has been properly fitted to the arm. By using two sensors 322a-322b distributed across the perimeter of the inside of the sleeve (e.g. one on the front side of the arm and one on the back side of the arm) at the first end (and a similar arrangement in the middle and at the second end) it can be detected that the body portion fills the sleeve 102, preventing a user from arranging the sleeve around a smaller portion of the body that only partly fits the sleeve. It is recognized that the number of sensors and their arrangement may vary depending on the application and that the accuracy can be further improved by additional sensors. Through the sensors, it can also be ensured that the wearable TENS-device actually is in contact with the skin of the user and not with some other material. One way to implement such a skin detector is to measure a biophysical property by means of which the human skin can be characterized, such as the scattering coefficient and/or the absorption coefficient of the skin for light of a predetermined wavelength. For a detailed explanation of such a detector reference is made to WO02/078559 A1. Other alternatives are to measure the photo pletysmography to detect the presence of a blood flow, or perform electrical measurements.

According to an embodiment, the wearable TENS-device is provided with hinges 318a-b and locking means 320a-b as illustrated in FIG. 3. This enables an openable wearable TENS-device 100 that is easy to take on and off for the user. The locking means 320a-b which secures the sleeve 102 around the arm of the user preferably has a 'closure' indicator to make sure the sleeve is closed before electro stimulation begins. The 'closure indicator' may simply be an electric switch which closes the circuit as the wearable sleeve is closed. An openable wearable TENS-device 100, enables the use of rigid materials therein. The use of rigid materials for the wearable TENS-device 100 may be advantageous as it makes it harder to fit the wearable TENS-device 100 to a portion of the body for which the wearable device is not intended. However, an elastic material may provide a better fit and typically makes it easier to adjust the wearable TENS-device to accommodate various body sizes.

The skilled person realizes that the present invention by no means is limited to the preferred embodiments described above. On the contrary, many modifications and variations are possible within the scope of the appended claims. For example, the device is not restricted to use by humans, but may be utilized for animals, such as, for example, horses.

The invention claimed is:

1. A wearable device for electric stimulation of a body of a user, wherein the wearable device is adapted to fit a portion of the body of the user, the wearable device comprising;
   at least one electrode embedded in the wearable device for transferring a stimulating current to the body of the user;
   a connection point being an intermediate connection between the at least one electrode and a control unit, the control unit being adapted to generate the stimulating current; and
   a detector configured to detect whether a change in a physical relationship between the connection point and the at least one electrode exceeds a predetermined threshold value, thereby enabling detection of misuse and tampering with the device, wherein the physical relationship between the connection point and the at least one electrode includes a relative position between the connection point and the at least one electrode.

2. The wearable device according to claim 1, further comprising at least one electrical wire embedded in the wearable device and providing an electrical connection from the connection point to the at least one electrode, wherein a length of the at least one electrical wire is at least twice a distance between the connection point and the electrode.

3. The wearable device according to claim 1, wherein the wearable device encompasses the portion of the body of the user which the wearable device is adapted to fit.

4. The wearable device according to claim 3, wherein the at least one electrical wire is circumferentially arranged.

5. The wearable device according to claim 1, wherein the wearable device has a sleeve-shaped form adapted to fit a portion of an arm or a leg of the user.

6. The wearable: device according to claim 1, wherein the wearable device is a garment.

7. The wearable device a according to claim 1, wherein the at least one electrical wire comprises electrical wires that cross one another while remaining electrically insulated.

8. The wearable device according to claim 1, wherein the wearable device is openable and provided with lock usable to ensure that the wearable device is closed before the stimulating current is provided, wherein the lock comprises an electric switch which closes a circuit and allows application of the stimulating current.

9. The wearable device according to claim 1, wherein the control unit
contains a predetermined reference key unique to the wearable device;
is configured to measure a parameter for the at least one electrical wire; and
is further configured to calculate a key based on the at least one measured parameter, wherein the calculated key is usable for ensuring proper functioning of the wearable device by comparing the calculated key with the predetermined reference key.

10. The wearable device of claim 9, wherein the parameter includes at least of one of capacitance, inductance, and resistance between the different wires of the at least one electrical wire measure at predetermined frequencies.

11. The wearable device according to claim 1, comprising an additional sensing wire monitored by the control unit.

12. The wearable device according to claim 11, wherein a plurality of sensing wires forms a mesh usable to locate a change in position of the at least one electrode.

13. The wearable device according to claim 1, wherein each electrical wire is arranged in a different layer in such a way that the electrical wires cross one another while remaining electrically insulated.

14. The wearable device according to claim 1, further comprising at least one sensor configured to detect contact with a skin of the user.

15. The wearable device claim 1, wherein the wearable device comprises two sections that are hingedly connected to allow opening the wearable device for fitting on the portion of the body of the user, the wearable device further comprising a lock usable to ensure that the wearable device is closed before the stimulating current is provided, wherein the lock comprises an electric switch which closes a circuit as the wearable sleeve is closed and allows application of the stimulating current.

16. A system for electrically stimulating a body of a user, comprising:
a control unit for generating a stimulating current; and
a wearable device for transferring the stimulating current to the user's body, wherein the wearable device comprises:
at least one electrode embedded in the wearable device for transferring a stimulating current to the body or the user;
a connection point being an intermediate connection between the at least one electrode and control unit, the control unit being adapted to generate the stimulating current; and
a detector configured to detect whether a change in a physical relationship between the connection point and the at least one electrode exceeds a predetermined threshold value, thereby enabling detection of misuse and tampering with the device, wherein the physical relationship between the connection point and the at least one electrode includes a relative position between the connection point and the at least one electrode.

17. The system of claim 16, wherein the wearable device further comprises at least one electrical wire embedded in the wearable device and providing an electrical connection from the connection point to the at least one electrode, wherein a length of the at least one electrical wire is at least twice a distance between the connection point and the electrode.

18. The system of claim 16, wherein the control unit
contains e predetermined reference key unique to the wearable device;
is configured to measure a parameter for the at least one electrical wire; and
is further configured to calculate a key based on the at least one measured parameter, wherein the calculated key is usable for ensuring proper functioning of the wearable device by comparing the calculated key with the predetermined reference key.

19. The system of claim 18, wherein the parameter includes at least one of capacitance, inductance, and resistance between the different wires of the at least one electrical wire measured at predetermined frequencies.

20. The system of claim 16, wherein the wearable device comprises two sections that are hingedly connected to allow opening the wearable device for fitting on the portion of the body of the user, the wearable device further comprising a lock usable to ensure that the wearable device is closed before the stimulating current is provided, wherein the look comprises an electric switch which closes a circuit as the wearable sleeve is closed and allows application of the stimulating current.

* * * * *